US010644514B2

(12) United States Patent
Hansen

(10) Patent No.: US 10,644,514 B2
(45) Date of Patent: May 5, 2020

(54) RESONANT POWER TRANSFER SYSTEMS WITH PROTECTIVE ALGORITHM

(71) Applicant: TC1 LLC, St. Paul, MN (US)

(72) Inventor: John Freddy Hansen, Pleasanton, CA (US)

(73) Assignee: TC1 LLC, St. Paul, MN (US)

( * ) Notice: Subject to any disclaimer, the term of this patent is extended or adjusted under 35 U.S.C. 154(b) by 0 days.

(21) Appl. No.: 16/355,034

(22) Filed: Mar. 15, 2019

(65) Prior Publication Data

US 2019/0214830 A1 Jul. 11, 2019

Related U.S. Application Data

(63) Continuation of application No. 15/783,132, filed on Oct. 13, 2017, now Pat. No. 10,277,039, which is a continuation of application No. 14/414,832, filed as application No. PCT/US2013/052542 on Jul. 29, 2013, now Pat. No. 9,825,471.

(Continued)

(51) Int. Cl.
*H02J 5/00* (2016.01)
*H02J 50/12* (2016.01)
*H02J 50/60* (2016.01)
*H02J 7/02* (2016.01)
*A61B 5/00* (2006.01)

(52) U.S. Cl.
CPC ............. *H02J 5/005* (2013.01); *H02J 7/025* (2013.01); *H02J 50/12* (2016.02); *H02J 50/60* (2016.02); *A61B 5/74* (2013.01)

(58) Field of Classification Search
USPC ........................................................ 307/104
See application file for complete search history.

(56) References Cited

U.S. PATENT DOCUMENTS 4,041,955 A 8/1977 Kelly et al.
4,352,960 A 10/1982 Dormer et al.
(Continued)

FOREIGN PATENT DOCUMENTS

DE 202012000166 U1 6/2013
DE 102012201073 B4 5/2014
(Continued)

OTHER PUBLICATIONS

Development and Implementation of RFID Technology, Ed. Cristina Turcu, Feb. 2009, pp. 28-30, 93-97.
(Continued)

*Primary Examiner* — Hal Kaplan
*Assistant Examiner* — Xuan Ly
(74) *Attorney, Agent, or Firm* — Armstrong Teasdale LLP

(57) ABSTRACT

Systems for tuning a wireless power transfer system are provided, which may include any number of features. In one embodiment, a TET system includes a receive resonator is adapted to be implanted in a human patient and is configured to receive wireless power from a transmit resonator. The system can include a controller configured to identify if a foreign object is interfering with the transmission of power or generating an induced voltage in the receive resonator. The controller can also be configured to control the transmit resonator to phase match with the foreign object. Methods of use are also provided.

11 Claims, 4 Drawing Sheets

Related U.S. Application Data

(60) Provisional application No. 61/676,699, filed on Jul. 27, 2012.

(56) References Cited

U.S. PATENT DOCUMENTS

| | | |
|---|---|---|
| 4,561,443 A | 12/1985 | Hogrefe et al. |
| 4,561,444 A | 12/1985 | Livingston et al. |
| 4,630,615 A | 12/1986 | Yomtov |
| 4,679,560 A | 7/1987 | Galbraith |
| 4,726,378 A | 2/1988 | Kaplan |
| 4,736,747 A | 4/1988 | Drake |
| 4,924,171 A | 5/1990 | Baba et al. |
| 4,945,305 A | 7/1990 | Blood |
| 5,070,223 A | 12/1991 | Colasante |
| 5,346,458 A | 9/1994 | Affeld |
| 5,350,413 A | 9/1994 | Miller |
| 5,569,156 A | 10/1996 | Mussivand |
| 5,630,836 A | 5/1997 | Prem et al. |
| 5,690,693 A | 11/1997 | Wang et al. |
| 5,702,431 A | 12/1997 | Wang et al. |
| 5,755,748 A | 5/1998 | Borza |
| 5,771,438 A | 6/1998 | Palermo et al. |
| 5,831,248 A | 11/1998 | Hojyo et al. |
| 5,948,006 A | 9/1999 | Mann |
| 6,123,726 A | 9/2000 | Mori et al. |
| 6,149,683 A | 11/2000 | Lancisi et al. |
| 6,212,430 B1 | 4/2001 | Kung |
| 6,296,533 B1 | 10/2001 | Grubbs et al. |
| 6,312,338 B1 | 11/2001 | Sato et al. |
| 6,320,354 B1 | 11/2001 | Sengupta et al. |
| 6,324,431 B1 | 11/2001 | Zarinetchi et al. |
| 6,327,504 B1 | 12/2001 | Dolgin et al. |
| 6,389,318 B1 | 5/2002 | Zarinetchi et al. |
| 6,400,991 B1 | 6/2002 | Kung |
| 6,442,434 B1 | 8/2002 | Zarinetchi et al. |
| 6,451,055 B1 | 9/2002 | Weiss |
| 6,458,164 B1 | 10/2002 | Weiss |
| 6,478,820 B1 | 11/2002 | Weiss |
| 6,553,263 B1 | 4/2003 | Meadows et al. |
| 6,579,315 B1 | 6/2003 | Weiss |
| 6,591,139 B2 | 7/2003 | Loftin et al. |
| 6,605,032 B2 | 8/2003 | Benkowski et al. |
| 6,647,298 B2 | 11/2003 | Abrahamson et al. |
| 6,650,213 B1 | 11/2003 | Sakurai et al. |
| 6,723,039 B2 | 4/2004 | French et al. |
| 6,772,011 B2 | 8/2004 | Dolgin |
| 6,801,807 B2 | 10/2004 | Abrahamson |
| 6,810,289 B1 | 10/2004 | Shaquer |
| 6,850,803 B1 | 2/2005 | Jimenez et al. |
| 6,894,456 B2 | 5/2005 | Tsukamoto et al. |
| 6,895,281 B1 | 5/2005 | Amundson et al. |
| 6,949,065 B2 | 9/2005 | Sporer et al. |
| 6,960,968 B2 | 11/2005 | Odendaal et al. |
| 6,967,621 B1 | 11/2005 | Cadotte, Jr. et al. |
| 6,985,773 B2 | 1/2006 | Von Arx et al. |
| 7,015,769 B2 | 3/2006 | Schulman et al. |
| 7,107,103 B2 | 9/2006 | Schulman et al. |
| 7,126,310 B1 | 10/2006 | Barron |
| 7,225,032 B2 | 5/2007 | Schmeling et al. |
| 7,246,040 B2 | 7/2007 | Borg et al. |
| 7,286,880 B2 | 10/2007 | Olson et al. |
| 7,428,438 B2 | 9/2008 | Parramon et al. |
| 7,471,986 B2 | 12/2008 | Hatlestad |
| 7,496,733 B2 | 2/2009 | Altman et al. |
| 7,505,816 B2 | 3/2009 | Schmeling et al. |
| 7,515,012 B2 | 4/2009 | Schulman et al. |
| 7,522,878 B2 | 4/2009 | Baarman |
| 7,532,901 B1 | 5/2009 | LaFranchise et al. |
| 7,565,187 B1 | 7/2009 | Dynok et al. |
| 7,571,007 B2 | 8/2009 | Erickson et al. |
| 7,574,173 B2 | 8/2009 | Terranova et al. |
| 7,587,241 B2 | 9/2009 | Parramon et al. |
| 7,599,743 B2 | 10/2009 | Hassler et al. |
| 7,650,187 B2 | 1/2010 | Gruber et al. |
| 7,650,192 B2 | 1/2010 | Wahlstrand |
| 7,711,433 B2 | 5/2010 | Davis et al. |
| 7,720,546 B2 | 5/2010 | Ginggen et al. |
| 7,741,734 B2 | 6/2010 | Joannopoulos et al. |
| 7,761,164 B2 | 7/2010 | Verhoef et al. |
| 7,774,069 B2 | 8/2010 | Olson et al. |
| 7,782,190 B1 | 8/2010 | Martin et al. |
| 7,805,200 B2 | 9/2010 | Kast et al. |
| 7,812,481 B2 | 10/2010 | Iisaka et al. |
| 7,818,036 B2 | 10/2010 | Lair et al. |
| 7,818,037 B2 | 10/2010 | Lair et al. |
| 7,825,543 B2 | 11/2010 | Karalis et al. |
| 7,830,114 B2 | 11/2010 | Reed |
| 7,865,245 B2 | 1/2011 | Torgerson et al. |
| 7,872,367 B2 | 1/2011 | Recksiek et al. |
| 7,904,170 B2 | 3/2011 | Harding |
| 7,932,696 B2 | 4/2011 | Peterson |
| 7,962,222 B2 | 6/2011 | He et al. |
| RE42,682 E | 9/2011 | Barreras et al. |
| 8,076,801 B2 | 12/2011 | Karalis et al. |
| 8,081,925 B2 | 12/2011 | Parramon et al. |
| 8,096,954 B2 | 1/2012 | Stahmann et al. |
| 8,140,168 B2 | 3/2012 | Olson et al. |
| 8,150,529 B2 | 4/2012 | Snell et al. |
| 8,165,694 B2 | 4/2012 | Carbanaru et al. |
| 8,185,212 B2 | 5/2012 | Carbunaru et al. |
| 8,193,766 B2 | 6/2012 | Rondoni et al. |
| 8,203,434 B2 | 6/2012 | Yoshida |
| 8,244,367 B2 | 8/2012 | Wahlstrand et al. |
| 8,247,926 B2 | 8/2012 | Issa et al. |
| 8,258,653 B2 | 9/2012 | Kitamura et al. |
| 8,265,770 B2 | 9/2012 | Toy et al. |
| 8,278,784 B2 | 10/2012 | Cook et al. |
| 8,292,052 B2 | 10/2012 | Bohori et al. |
| 8,299,652 B2 | 10/2012 | Sample et al. |
| 8,301,079 B2 | 10/2012 | Baarman |
| 8,319,473 B2 | 11/2012 | Choi et al. |
| 8,362,742 B2 | 1/2013 | Kallmyer |
| 8,373,310 B2 | 2/2013 | Baarman et al. |
| 8,378,522 B2 | 2/2013 | Cook et al. |
| 8,378,523 B2 | 2/2013 | Cook et al. |
| 8,463,395 B2 | 6/2013 | Forsell |
| 8,489,200 B2 | 7/2013 | Zarinetchi et al. |
| 8,551,163 B2 | 10/2013 | Aber et al. |
| 8,562,508 B2 | 10/2013 | Dague et al. |
| 8,581,793 B2 | 11/2013 | Carr |
| 8,587,154 B2 | 11/2013 | Fells et al. |
| 8,620,447 B2 | 12/2013 | D'Ambrosio et al. |
| 8,628,460 B2 | 1/2014 | Yomtov et al. |
| 8,629,578 B2 | 1/2014 | Kurs et al. |
| 8,668,473 B2 | 3/2014 | Larose et al. |
| 8,694,117 B2 | 4/2014 | Aghassian et al. |
| 8,810,071 B2 | 8/2014 | Sauerlaender et al. |
| 8,884,468 B2 | 11/2014 | Lemmens et al. |
| 8,909,351 B2 | 12/2014 | Dinsmoor et al. |
| 8,971,958 B2 | 3/2015 | Frikart et al. |
| 9,002,468 B2 | 4/2015 | Shea et al. |
| 9,106,083 B2 | 8/2015 | Partovi |
| 9,192,704 B2 | 11/2015 | Yomtov et al. |
| 9,302,093 B2 | 4/2016 | Mashiach |
| 9,515,494 B2 | 12/2016 | Kurs et al. |
| 9,515,495 B2 | 12/2016 | Kurs et al. |
| 9,560,787 B2 | 1/2017 | Kallmyer et al. |
| 2002/0038138 A1 | 3/2002 | Zarinetchi et al. |
| 2002/0087204 A1 | 7/2002 | Kung et al. |
| 2002/0093456 A1 | 7/2002 | Sawamura et al. |
| 2002/0151770 A1 | 10/2002 | Noll, III |
| 2003/0085684 A1 | 5/2003 | Tsukamoto et al. |
| 2003/0109910 A1 | 6/2003 | Lachenbruch et al. |
| 2003/0171792 A1 | 9/2003 | Zarinetchi et al. |
| 2004/0106963 A1 | 6/2004 | Tsukamoto et al. |
| 2004/0138725 A1 | 7/2004 | Forsell |
| 2004/0256146 A1 | 12/2004 | Frericks |
| 2005/0006083 A1 | 1/2005 | Chen et al. |
| 2005/0021100 A1 | 1/2005 | Tsukamoto et al. |
| 2005/0288743 A1 | 12/2005 | Ahn et al. |
| 2006/0156756 A1 | 7/2006 | Becke |
| 2006/0191344 A1 | 8/2006 | Hashimoto |
| 2006/0199997 A1 | 9/2006 | Hassler et al. |
| 2006/0247737 A1 | 11/2006 | Olson et al. |

(56) References Cited

U.S. PATENT DOCUMENTS

| | | |
|---|---|---|
| 2006/0247738 A1 | 11/2006 | Schmeling et al. |
| 2006/0271129 A1 | 11/2006 | Tai et al. |
| 2007/0096686 A1 | 5/2007 | Jimenez et al. |
| 2007/0123948 A1 | 5/2007 | Dal Molin |
| 2007/0142696 A1 | 6/2007 | Crosby et al. |
| 2007/0167997 A1 | 7/2007 | Forsberg |
| 2007/0191706 A1 | 8/2007 | Calderon et al. |
| 2008/0009198 A1 | 1/2008 | Marino |
| 2008/0027293 A1 | 1/2008 | Vodermayer et al. |
| 2008/0087270 A1 | 4/2008 | Shaikh et al. |
| 2008/0100294 A1 | 5/2008 | Rohling et al. |
| 2008/0149736 A1 | 6/2008 | Kim et al. |
| 2008/0167531 A1 | 7/2008 | McDermott |
| 2008/0197126 A1 | 8/2008 | Bourke et al. |
| 2008/0211320 A1 | 9/2008 | Cook et al. |
| 2008/0221555 A1 | 9/2008 | Sheppard et al. |
| 2009/0005770 A1 | 1/2009 | Gerber et al. |
| 2009/0018616 A1 | 1/2009 | Quick et al. |
| 2009/0051224 A1 | 2/2009 | Cook et al. |
| 2009/0072628 A1 | 3/2009 | Cook et al. |
| 2009/0081943 A1 | 3/2009 | Dobyns et al. |
| 2009/0112291 A1 | 4/2009 | Wahlstrand et al. |
| 2009/0157148 A1 | 6/2009 | Phillips |
| 2009/0174264 A1* | 7/2009 | Onishi ............ H02J 5/005 307/104 |
| 2009/0212736 A1 | 8/2009 | Baarman et al. |
| 2009/0226328 A1 | 9/2009 | Morello |
| 2009/0270679 A1 | 10/2009 | Hoeg et al. |
| 2009/0284220 A1 | 11/2009 | Toncich et al. |
| 2010/0019985 A1 | 1/2010 | Bashyam et al. |
| 2010/0033021 A1 | 2/2010 | Bennett |
| 2010/0035453 A1 | 2/2010 | Tronnes et al. |
| 2010/0045114 A1 | 2/2010 | Sample et al. |
| 2010/0063347 A1 | 3/2010 | Yomtov et al. |
| 2010/0066305 A1 | 3/2010 | Takahashi et al. |
| 2010/0069992 A1 | 3/2010 | Aghassian et al. |
| 2010/0109958 A1 | 5/2010 | Haubrich et al. |
| 2010/0114143 A1 | 5/2010 | Albrecht et al. |
| 2010/0122995 A1 | 5/2010 | Thomas et al. |
| 2010/0171368 A1 | 7/2010 | Schatz et al. |
| 2010/0174201 A1 | 7/2010 | Bodecker et al. |
| 2010/0184371 A1 | 7/2010 | Cook et al. |
| 2010/0194334 A1 | 8/2010 | Kirby et al. |
| 2010/0210233 A1 | 8/2010 | Cook et al. |
| 2010/0211134 A1 | 8/2010 | Forsell |
| 2010/0222848 A1 | 9/2010 | Forsell |
| 2010/0222849 A1 | 9/2010 | Forsell |
| 2010/0225174 A1 | 9/2010 | Jiang |
| 2010/0230653 A1 | 9/2010 | Chen |
| 2010/0241194 A1 | 9/2010 | Kast et al. |
| 2010/0244576 A1 | 9/2010 | Hillan et al. |
| 2010/0253340 A1 | 10/2010 | Corum et al. |
| 2010/0256708 A1 | 10/2010 | Thornton et al. |
| 2010/0268305 A1 | 10/2010 | Olson |
| 2010/0274308 A1 | 10/2010 | Scott |
| 2010/0277121 A1 | 11/2010 | Hall et al. |
| 2010/0308939 A1 | 12/2010 | Kurs |
| 2010/0314946 A1 | 12/2010 | Budde et al. |
| 2010/0331919 A1 | 12/2010 | DiGiore et al. |
| 2011/0022125 A1 | 1/2011 | Olson |
| 2011/0025132 A1 | 2/2011 | Sato |
| 2011/0043050 A1 | 2/2011 | Yabe et al. |
| 2011/0046699 A1 | 2/2011 | Mazanec |
| 2011/0057607 A1 | 3/2011 | Carobolante |
| 2011/0087192 A1 | 4/2011 | Uhland et al. |
| 2011/0100495 A1 | 5/2011 | Welle |
| 2011/0101790 A1 | 5/2011 | Budgett |
| 2011/0106213 A1 | 5/2011 | Davis |
| 2011/0109263 A1 | 5/2011 | Sakoda et al. |
| 2011/0115431 A1 | 5/2011 | Dunworth et al. |
| 2011/0118661 A1 | 5/2011 | Pless et al. |
| 2011/0120673 A1 | 5/2011 | Xiang |
| 2011/0127848 A1 | 6/2011 | Ryu et al. |
| 2011/0148215 A1 | 6/2011 | Marzetta et al. |
| 2011/0172744 A1 | 7/2011 | Davis et al. |
| 2011/0175568 A1 | 7/2011 | Leijssen |
| 2011/0178361 A1 | 7/2011 | Yomtov |
| 2011/0181235 A1 | 7/2011 | Walley et al. |
| 2011/0205083 A1 | 8/2011 | Janna et al. |
| 2011/0234155 A1 | 9/2011 | Chen et al. |
| 2011/0241436 A1 | 10/2011 | Furukawa |
| 2011/0245892 A1 | 10/2011 | Kast et al. |
| 2011/0266880 A1 | 11/2011 | Kim et al. |
| 2011/0276110 A1 | 11/2011 | Whitehurst et al. |
| 2011/0278948 A1 | 11/2011 | Forsell |
| 2011/0291489 A1 | 12/2011 | Tsai et al. |
| 2011/0291613 A1 | 12/2011 | Rosik et al. |
| 2011/0295345 A1 | 12/2011 | Wells et al. |
| 2011/0298294 A1 | 12/2011 | Takada et al. |
| 2011/0301667 A1 | 12/2011 | Olson et al. |
| 2011/0313238 A1 | 12/2011 | Reichenbach et al. |
| 2012/0001485 A1 | 1/2012 | Uchida |
| 2012/0001493 A1* | 1/2012 | Kudo .............. H02J 5/005 307/104 |
| 2012/0032522 A1 | 2/2012 | Schatz et al. |
| 2012/0039102 A1 | 2/2012 | Shinoda |
| 2012/0057322 A1 | 3/2012 | Waffenschmidt |
| 2012/0065458 A1 | 3/2012 | Tol |
| 2012/0080957 A1 | 4/2012 | Cooper et al. |
| 2012/0091951 A1 | 4/2012 | Sohn |
| 2012/0104997 A1* | 5/2012 | Carobolante ........ H02J 7/025 320/108 |
| 2012/0109256 A1 | 5/2012 | Meskins et al. |
| 2012/0119914 A1 | 5/2012 | Uchida |
| 2012/0146575 A1 | 6/2012 | Armstrong et al. |
| 2012/0149229 A1 | 6/2012 | Kearsley et al. |
| 2012/0150259 A1 | 6/2012 | Meskens |
| 2012/0153954 A1 | 6/2012 | Ota et al. |
| 2012/0157753 A1 | 6/2012 | D'Ambrosio |
| 2012/0157754 A1 | 6/2012 | D'Ambrosio |
| 2012/0158407 A1 | 6/2012 | Forsell |
| 2012/0161539 A1 | 6/2012 | Kim et al. |
| 2012/0164943 A1 | 6/2012 | Bennett |
| 2012/0169132 A1 | 7/2012 | Choudhary et al. |
| 2012/0169133 A1 | 7/2012 | Lisi et al. |
| 2012/0169137 A1 | 7/2012 | Lisi et al. |
| 2012/0169139 A1 | 7/2012 | Kudo |
| 2012/0169278 A1 | 7/2012 | Choi et al. |
| 2012/0175967 A1 | 7/2012 | Dibben et al. |
| 2012/0235634 A1* | 9/2012 | Hall ................ H03H 7/40 320/108 |
| 2012/0239118 A1 | 9/2012 | Ozawa et al. |
| 2012/0245649 A1 | 9/2012 | Bohori et al. |
| 2012/0245664 A1 | 9/2012 | Smith et al. |
| 2012/0259398 A1 | 10/2012 | Chen et al. |
| 2012/0274148 A1 | 11/2012 | Sung et al. |
| 2012/0306433 A1 | 12/2012 | Kim et al. |
| 2013/0007949 A1 | 1/2013 | Kurs et al. |
| 2013/0060103 A1 | 3/2013 | Bergida et al. |
| 2013/0106347 A1 | 5/2013 | Kallmyer et al. |
| 2013/0119773 A1 | 5/2013 | Davis |
| 2013/0127253 A1 | 5/2013 | Stark et al. |
| 2013/0149960 A1 | 6/2013 | Dec et al. |
| 2013/0159956 A1 | 6/2013 | Verghese et al. |
| 2013/0190551 A1 | 7/2013 | Callaway et al. |
| 2013/0197607 A1 | 8/2013 | Wilder et al. |
| 2013/0214731 A1 | 8/2013 | Dinsmoor |
| 2013/0241306 A1 | 9/2013 | Aber et al. |
| 2013/0241468 A1 | 9/2013 | Moshfeghi |
| 2013/0271088 A1 | 10/2013 | Hwang et al. |
| 2013/0289334 A1 | 10/2013 | Badstibner et al. |
| 2013/0310630 A1 | 11/2013 | Smith et al. |
| 2013/0320773 A1 | 12/2013 | Schatz et al. |
| 2013/0331638 A1 | 12/2013 | Cameron et al. |
| 2014/0005466 A1 | 1/2014 | Crosby et al. |
| 2014/0011447 A1 | 1/2014 | Konanur et al. |
| 2014/0028110 A1 | 1/2014 | Petersen et al. |
| 2014/0028111 A1 | 1/2014 | Hansen et al. |
| 2014/0031606 A1 | 1/2014 | Hansen et al. |
| 2014/0152252 A1 | 6/2014 | Wood |
| 2014/0163644 A1 | 6/2014 | Scott et al. |
| 2014/0265620 A1 | 9/2014 | Hoarau et al. |
| 2014/0265621 A1 | 9/2014 | Wong et al. |
| 2014/0275727 A1 | 9/2014 | Bonde et al. |

(56) References Cited

U.S. PATENT DOCUMENTS

| | | |
|---|---|---|
| 2015/0123654 A1 | 5/2015 | Gagnon et al. |
| 2015/0180241 A1 | 6/2015 | Petersen et al. |
| 2015/0207330 A1 | 7/2015 | Petersen |
| 2015/0207331 A1 | 7/2015 | Petersen |
| 2015/0222128 A1 | 8/2015 | Hansen |
| 2015/0222139 A1 | 8/2015 | Petersen et al. |
| 2015/0229289 A1 | 8/2015 | Suzuki |
| 2015/0290373 A1 | 10/2015 | Rudser et al. |
| 2016/0135684 A1 | 5/2016 | Kappel et al. |
| 2016/0218432 A1 | 7/2016 | Pope et al. |
| 2016/0250484 A1 | 9/2016 | Nguyen et al. |
| 2016/0254703 A1 | 9/2016 | Hansen |
| 2016/0254704 A1 | 9/2016 | Hansen et al. |

FOREIGN PATENT DOCUMENTS

| | | | |
|---|---|---|---|
| EP | 1513241 A1 | | 3/2005 |
| JP | H03109063 A | | 3/1967 |
| JP | 11506646 A | | 6/1999 |
| JP | 2014160611 A | | 8/2013 |
| JP | 2013161640 A1 | | 12/2014 |
| JP | 2013094456 A1 | | 4/2015 |
| KR | 1020120007296 A | | 11/2002 |
| KR | 20120077448 A | | 1/2012 |
| KR | 20120077448 | * | 7/2012 |
| KR | 1020020089605 A | | 9/2014 |
| WO | 2000074747 A1 | | 3/1974 |
| WO | 0001442 A2 | | 1/2000 |
| WO | 137926 A1 | | 5/2001 |
| WO | 2005037365 A1 | | 4/2005 |
| WO | 2005106901 A2 | | 11/2005 |
| WO | 2007053881 A1 | | 5/2007 |
| WO | 2008066941 A2 | | 6/2008 |
| WO | 2009018271 A1 | | 2/2009 |
| WO | 2009021220 A1 | | 2/2009 |
| WO | 2009023905 A1 | | 2/2009 |
| WO | 2009029977 A1 | | 3/2009 |
| WO | 2009042977 A1 | | 4/2009 |
| WO | 2010030378 A1 | | 3/2010 |
| WO | 2010089354 A2 | | 8/2010 |
| WO | 2011081626 A1 | | 7/2011 |
| WO | 2011113934 A1 | | 9/2011 |
| WO | 2012002063 A1 | | 1/2012 |
| WO | 2012056365 A2 | | 5/2012 |
| WO | 2012087807 A2 | | 6/2012 |
| WO | 2012087811 A2 | | 6/2012 |
| WO | 2012087816 A2 | | 6/2012 |
| WO | 2012087819 A2 | | 6/2012 |
| WO | 2012099965 A2 | | 7/2012 |
| WO | 2012141752 A2 | | 10/2012 |
| WO | 2013110602 A1 | | 8/2013 |
| WO | 2013138451 A1 | | 9/2013 |
| WO | 2014039673 A1 | | 3/2014 |

OTHER PUBLICATIONS

Merli, Francesco, et al., "Design, Realization and Measurements of a Miniature Antenna for Implantable Wireless Communication Systems", IEEE Transaction on Antennas and Propagation, vol. 59, No. 10, Oct. 2011, pp. 3544-3555.

Merli, Francesco, et al.,"The Effect of Insulating Layers on the Performance of Implanted Antennas", IEEE Transaction on Antennas and Propagation, vol. 59, No. 1, Jan. 2011, pp. 21-31.

Abadia, Javier, et al., 3D-Spiral Small Antenna Design and Realization for Biomdical Telemetry in the MICS Band. Radioengineering, vol. 18, No. 4, Dec. 2009, pp. 359-367.

Notification of Transmittal of the International Search Report and the Written Opinion of the International Searching Authority for PCT Application No. PCT/US2015/051474, dated Dec. 30, 2015.

Motavalli, Jim; WiTricity Takes Its Car-Charging Technology Out for a Road Test; New York Times; 3 pgs.; Jul. 25, 2012; retrieved Mar. 12, 2014 from the internet: http://wheels.blogs.nytimes.com/2012/07/25/witricity-takes-its-car-chargi-ng-technology-out-for-a-road-test/.

Ferret, B.; Electric vehicles get big boost!; Renewable Energy World; 3 pgs.; Jul. 30, 2012; retrieved Jul. 30, 2012 from the internet: http://www.renewableenergyworld.com/rea/blog/post/2012/07/.

Evatran; PluglessTM Level 2 EV Charging System (3.3kW); product brochure; 7 pgs.; retrieved Mar. 12, 2014 from the internet: http://www.pluglesspower.com/tech-specs/.

Dixon, Jr.; Eddy current losses in transformer windings and circuit wiring; Unitrode Corp. Seminar Manual (SEM600); Watertown, MA; 12 pgs.; 1988 (year of pub. sufficiently earlier than effective US filing date and any foreign priority date).

Chargepoint, Inc.; −chargepoin+.RTM.; product brochure; 4 pgs.; .COPYRGT. 2014; retrieved Mar. 12, 2014 from the internet: http://www.chargepoint.com/network/.

Bonde et al.; Promise of unrestricted mobility with innovative, portable wireless powering of a mechanical circulatory assist device; American Association for Thoracic Surgery; .COPYRGT. 2012; 2 pgs.; retrieved Mar. 12, 2014 from the internet: http://aats.org/annualmeeting/Abstracts/2012/T8.cgi.

* cited by examiner $$k \approx \frac{A_2}{A_1} \cos\Theta$$

RESONANT POWER TRANSFER SYSTEMS WITH PROTECTIVE ALGORITHM

CROSS-REFERENCE TO RELATED APPLICATIONS

This application is a Continuation of U.S. patent application Ser. No. 15/783,132 filed on Oct. 13, 2017, which is a Continuation of U.S. patent application Ser. No. 14/414, 832 filed on Jan. 14, 2015, now issued U.S. Pat. No. 9,825,471, which is a National Stage Application claiming priority to International Patent Application No. PCT/US2013/052542 filed on Jul. 29, 2013, which claims the benefit of priority to U.S. Provisional Patent Application No. 61/676,699 filed on Jul. 27, 2012, each of which is hereby incorporated herein by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure relates generally to methods and apparatus for transmitting and receiving power wirelessly, and in various respects, mechanical circulatory support.

BACKGROUND

Powered devices need to have a mechanism to supply power to the operative parts. Typically systems use a physical power cable to transfer energy over a distance. There has been a continuing need for systems that can transmit power efficiently over a distance without physical structures bridging the physical gap.

Systems and methods that supply power without electrical wiring are sometimes referred to as wireless energy transmission (WET). Wireless energy transmission greatly expands the types of applications for electrically powered devices. One such example is the field of implantable medical devices. Implantable medical devices typically require an internal power source able to supply adequate power for the reasonable lifetime of the device or an electrical cable that traverses the skin. Typically an internal power source (e.g. battery) is feasibly for only low power devices like sensors. Likewise, a transcutaneous power cable significantly affects quality of life (QoL), infection risk, and product life, among many drawbacks.

More recently there has been an emphasis on systems that supply power to an implanted device without using transcutaneous wiring. This is sometimes referred to as a Transcutaneous Energy Transfer System (TETS). Frequently energy transfer is accomplished using two magnetically coupled coils set up like a transformer so power is transferred magnetically across the skin. Conventional systems are relatively sensitive to variations in position and alignment of the coils. In order to provide constant and adequate power, the two coils need to be physically close together and well aligned.

A problem can occur when a TET system interacts with other TET systems and/or materials with magnetic susceptibility. For example, there is risk of interference with a TET system if the user gets into a car. A metal object essentially changes the inductance and characteristics of the circuit. Another risk involves two users with TET systems getting near each other. These problems must be solved to ensure the safety of users with implanted TET systems.

SUMMARY OF THE DISCLOSURE

A method of protecting a wireless power transfer system from foreign interference is provided, comprising the steps of transmitting wireless power from a transmit resonator to a receive resonator implanted in a human patient, identifying if a foreign object is interfering with the transmission of power or generating an induced voltage in the receive resonator, and if a foreign object is interfering with the transmission of power, controlling the transmit resonator to phase match with the foreign object.

In some embodiments, the method further comprises indicating to the patient whether the foreign object is interfering with transmission of power.

In one embodiment, the identifying step further comprises halting the transmission of power, then determining if the receive resonator picks a foreign wireless power signal.

In another embodiment, the identifying step further comprises detecting a return energy transmitted from the receive resonator to the transmit resonator, and comparing the return energy to an expected return energy value.

In some embodiments, the identifying step further comprises identifying that the foreign object is interfering with the transmission of power by detecting a wireless power signal in the receive resonator in approximately the same frequency band as an operating frequency of the wireless power transfer system.

A wireless power transfer system is also provided, comprising a transmit resonator configured to transmit wireless power a receive resonator adapted to be implanted in a human patient and configured to receive wireless power from the transmit resonator, and a controller configured to identify if a foreign object is interfering with the transmission of power or generating an induced voltage in the receive resonator, the controller configured to control the transmit resonator to phase match with the foreign object.

In some embodiments, the controller is a transmit controller connected to the transmit resonator.

In another embodiment, the controller is a receive controller connected to the receive resonator.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
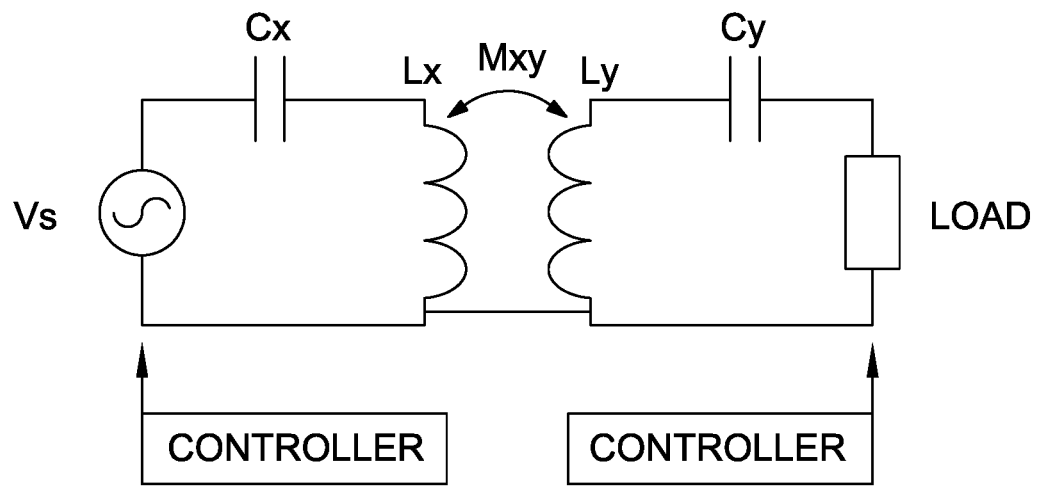
FIG. 1 illustrates a basic wireless power transfer system.

In the description that follows, like components have been given the same reference numerals, regardless of whether they are shown in different embodiments. To illustrate an embodiment(s) of the present disclosure in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

Various aspects of the invention are similar to those described in International Patent Pub. No. WO2012045050; U.S. Pat. Nos. 8,140,168; 7,865,245; 7,774,069; 7,711,433; 7,650,187; 7,571,007; 7,741,734; 7,825,543; 6,591,139; 6,553,263; and 5,350,413; and U.S. Pub. Nos. 2010/0308939; 2008/027293; and 2010/0102639, the entire contents of which patents and applications are incorporated herein for all purposes.

Wireless Power Transmission System

Power may be transmitted wirelessly by magnetic induction. In various embodiments, the transmitter and receiver are closely coupled.

In some cases "closely coupled" or "close coupling" refers to a system that requires the coils to be very near each other in order to operate. In some cases "loosely coupled" or "loose coupling" refers to a system configured to operate when the coils have a significant spatial and/or axial separation, and in some cases up to distance equal to or less than the diameter of the larger of the coils. In some cases, "loosely coupled" or "loose coupling" refers a system that is relatively insensitive to changes in physical separation and/or orientation of the receiver and transmitter.

In various embodiments, the transmitter and receiver are non-resonant coils. For example, a change in current in one coil induces a changing magnetic field. The second coil within the magnetic field picks up the magnetic flux, which in turn induces a current in the second coil. An example of a closely coupled system with non-resonant coils is described in International Pub. No. WO2000/074747, incorporated herein for all purposes by reference. A conventional transformer is another example of a closely coupled, non-resonant system. In various embodiments, the transmitter and receiver are resonant coils. For example, one or both of the coils is connected to a tuning capacitor or other means for controlling the frequency in the respective coil. An example of closely coupled system with resonant coils is described in International Pub. Nos. WO2001/037926; WO2012/087807; WO2012/087811; WO2012/087816; WO2012/087819; WO2010/030378; and WO2012/056365, and U.S. Pub. No. 2003/0171792, incorporated herein for all purposes by reference.

In various embodiments, the transmitter and receiver are loosely coupled. For example, the transmitter can resonate to propagate magnetic flux that is picked up by the receiver at relatively great distances. In some cases energy can be transmitted over several meters. In a loosely coupled system power transfer may not necessarily depend on a critical distance. Rather, the system may be able to accommodate changes to the coupling coefficient between the transmitter and receiver. An example of a loosely coupled system is described in International Pub. No. WO2012/045050, incorporated herein for all purposes by reference.

Power may be transmitted wirelessly by radiating energy. In various embodiments, the system comprises antennas. The antennas may be resonant or non-resonant. For example, non-resonant antennas may radiate electromagnetic waves to create a field. The field can be near field or far field. The field can be directional. Generally far field has greater range but a lower power transfer rate. An example of such a system for radiating energy with resonators is described in International Pub. No. WO2010/089354, incorporated herein for all purposes by reference. An example of such a non-resonant system is described in International Pub. No. WO2009/018271, incorporated herein for all purposes by reference. Instead of antenna, the system may comprise a high energy light source such as a laser. The system can be configured so photons carry electromagnetic energy in a spatially restricted, direct, coherent path from a transmission point to a receiving point. An example of such a system is described in International Pub. No. WO2010/089354, incorporated herein for all purposes by reference.

Power may also be transmitted by taking advantage of the material or medium through which the energy passes. For example, volume conduction involves transmitting electrical energy through tissue between a transmitting point and a receiving point. An example of such a system is described in International Pub. No. WO2008/066941, incorporated herein for all purposes by reference.

Power may also be transferred using a capacitor charging technique. The system can be resonant or non-resonant. Exemplars of capacitor charging for wireless energy transfer are described in International Pub. No. WO2012/056365, incorporated herein for all purposes by reference.

The system in accordance with various aspects of the invention will now be described in connection with a system for wireless energy transfer by magnetic induction. The exemplary system utilizes resonant power transfer. The system works by transmitting power between the two inductively coupled coils. In contrast to a transformer, however, the exemplary coils are not coupled together closely. A transformer generally requires the coils to be aligned and positioned directly adjacent each other. The exemplary system accommodates looser coupling of the coils.

While described in terms of one receiver coil and one transmitter coil, one will appreciate from the description herein that the system may use two or more receiver coils and two or more transmitter coils. For example, the transmitter may be configured with two coils—a first coil to resonate flux and a second coil to excite the first coil. One will further appreciate from the description herein that usage of "resonator" and "coil" may be used somewhat interchangeably. In various respects, "resonator" refers to a coil and a capacitor connected together.

In accordance with various embodiments of this disclosure, the system comprises one or more transmitters configured to transmit power wirelessly to one or more receivers. In various embodiments, the system includes a transmitter and more than one receiver in a multiplexed arrangement. A frequency generator may be electrically coupled to the transmitter to drive the transmitter to transmit power at a particular frequency or range of frequencies. The frequency generator can include a voltage controlled oscillator and one or more switchable arrays of capacitors, a voltage controlled oscillator and one or more varactors, a phase-locked-loop, a direct digital synthesizer, or combinations thereof. The transmitter can be configured to transmit power at multiple frequencies simultaneously. The frequency generator can include two or more phase-locked-loops electrically coupled to a common reference oscillator, two or more independent voltage controlled oscillators, or combinations thereof. The transmitter can be arranged to simultaneously delivery power to multiple receivers at a common frequency.

In various embodiments, the transmitter is configured to transmit a low power signal at a particular frequency. The transmitter may transmit the low power signal for a particular time and/or interval. In various embodiments, the transmitter is configured to transmit a high power signal wirelessly at a particular frequency. The transmitter may transmit the high power signal for a particular time and/or interval.

In various embodiments, the receiver includes a frequency selection mechanism electrically coupled to the receiver coil and arranged to allow the resonator to change a frequency or a range of frequencies that the receiver can receive. The frequency selection mechanism can include a switchable array of discrete capacitors, a variable capacitance, one or more inductors electrically coupled to the receiving antenna, additional turns of a coil of the receiving antenna, or combinations thereof.

In general, most of the flux from the transmitter coil does not reach the receiver coil. The amount of flux generated by the transmitter coil that reaches the receiver coil is described by "k" and referred to as the "coupling coefficient."

In various embodiments, the system is configured to maintain a value of k in the range of between about 0.2 to about 0.01. In various embodiments, the system is configured to maintain a value of k of at least 0.01, at least 0.02, at least 0.03, at least 0.04, or at least 0.05.

In various embodiments, the coils are physically separated. In various embodiments, the separation is greater than a thickness of the receiver coil. In various embodiments, the separation distance is equal to or less than the diameter of the larger of the receiver and transmitter coil.

Because most of the flux does not reach the receiver, the transmitter coil must generate a much larger field than what is coupled to the receiver. In various embodiments, this is accomplished by configuring the transmitter with a large number of amp-turns in the coil.

Since only the flux coupled to the receiver gets coupled to a real load, most of the energy in the field is reactive. The current in the coil can be sustained with a capacitor connected to the coil to create a resonator. The power source thus only needs to supply the energy absorbed by the receiver. The resonant capacitor maintains the excess flux that is not coupled to the receiver.

In various embodiments, the impedance of the receiver is matched to the transmitter. This allows efficient transfer of energy out of the receiver. In this case the receiver coil may not need to have a resonant capacitor.

Turning now to FIG. 1, a simplified circuit for wireless energy transmission is shown. The exemplary system shows a series connection, but the system can be connected as either series or parallel on either the transmitter or receiver side.

The exemplary transmitter includes a coil Lx connected to a power source Vs by a capacitor Cx. The exemplary receiver includes a coil Ly connected to a load by a capacitor Cy. Capacitor Cx may be configured to make Lx resonate at a desired frequency. Capacitance Cx of the transmitter coil may be defined by its geometry. Inductors Lx and Ly are connected by coupling coefficient k. Mxy is the mutual inductance between the two coils. The mutual inductance, Mxy, is related to coupling coefficient, k.

$$Mxy = k\sqrt{Lx \cdot Ly}$$

In the exemplary system the power source Vs is in series with the transmitter coil Lx so it may have to carry all the reactive current. This puts a larger burden on the current rating of the power source and any resistance in the source will add to losses.

The exemplary system includes a receiver configured to receive energy wirelessly transmitted by the transmitter. The exemplary receiver is connected to a load. The receiver and load may be connected electrically with a controllable switch.

In various embodiments, the receiver includes a circuit element configured to be connected or disconnected from the receiver coil by an electronically controllable switch. The electrical coupling can include both a serial and parallel arrangement. The circuit element can include a resistor, capacitor, inductor, lengths of an antenna structure, or combinations thereof. The system can be configured such that power is transmitted by the transmitter and can be received by the receiver in predetermined time increments.

In various embodiments, the transmitter coil and/or the receiver coil is a substantially two-dimensional structure. In various embodiments, the transmitter coil may be coupled to a transmitter impedance-matching structure. Similarly, the receiver coil may be coupled to a receiver impedance-matching structure. Examples of suitable impedance-matching structures include, but are not limited to, a coil, a loop, a transformer, and/or any impedance-matching network. An impedance-matching network may include inductors or capacitors configured to connect a signal source to the resonator structure.

In various embodiments, the transmitter is controlled by a controller (not shown) and driving circuit. The controller and/or driving circuit may include a directional coupler, a signal generator, and/or an amplifier. The controller may be configured to adjust the transmitter frequency or amplifier gain to compensate for changes to the coupling between the receiver and transmitter.

In various embodiments, the transmitter coil is connected to an impedance-matched coil loop. The loop is connected to a power source and is configured to excite the transmitter coil. The first coil loop may have finite output impedance. A signal generator output may be amplified and fed to the transmitter coil. In use power is transferred magnetically between the first coil loop and the main transmitter coil, which in turns transmits flux to the receiver. Energy received by the receiver coil is delivered by Ohmic connection to the load.

One of the challenges to a practical circuit is how to get energy in and out of the resonators. Simply putting the power source and load in series or parallel with the resonators is difficult because of the voltage and current required. In various embodiments, the system is configured to achieve an approximate energy balance by analyzing the system characteristics, estimating voltages and currents involved, and controlling circuit elements to deliver the power needed by the receiver.

In an exemplary embodiment, the system load power, $P_L$, is assumed to be 15 Watts and the operating frequency of the system, f, is 250 kHz. Then, for each cycle the load removes a certain amount of energy from the resonance:

$$e_L = \frac{P_L}{f} = 60 \ \mu J \quad \text{Energy the load removes from one cycle}$$

$$e_L = \frac{P_L}{f} = 60 \ \mu J \quad \text{Energy the load removes in one cycle}$$

It has been found that the energy in the receiver resonance is typically several times larger than the energy removed by the load for operative, implantable medical devices. In various embodiments, the system assumes a ratio 7:1 for energy at the receiver versus the load removed. Under this assumption, the instantaneous energy in the exemplary receiver resonance is 420 µJ.

The exemplary circuit was analyzed and the self inductance of the receiver coil was found to be 60 uH. From the energy and the inductance, the voltage and current in the resonator could be calculated.

$$e_y = \frac{1}{2}Li^2$$

$$i_y = \sqrt{\frac{2e_y}{L}} = 3.74 \text{ A peak}$$

$$v_y = \omega L_y i_y = 352 \text{ V peak}$$

The voltage and current can be traded off against each other. The inductor may couple the same amount of flux regardless of the number of turns. The Amp-turns of the coil needs to stay the same in this example, so more turns means the current is reduced. The coil voltage, however, will need to increase. Likewise, the voltage can be reduced at the expense of a higher current. The transmitter coil needs to have much more flux. The transmitter flux is related to the receiver flux by the coupling coefficient. Accordingly, the energy in the field from the transmitter coil is scaled by k.

$$e_x = \frac{e_y}{k}$$

Given that k is 0.05:

$$e_x = \frac{420 \text{ µJ}}{0.05} = 8.4 \text{ mJ}$$

For the same circuit the self inductance of the transmitter coil was 146 uH as mentioned above. This results in:

$$i_x = \sqrt{\frac{2e_x}{L}} = 10.7 \text{ A peak}$$

$$v_x = \omega L_x i_x = 2460 \text{ V peak}$$

One can appreciate from this example, the competing factors and how to balance voltage, current, and inductance to suit the circumstance and achieve the desired outcome. Like the receiver, the voltage and current can be traded off against each other. In this example, the voltages and currents in the system are relatively high. One can adjust the tuning to lower the voltage and/or current at the receiver if the load is lower.

Estimation of Coupling Coefficient and Mutual Inductance

As explained above, the coupling coefficient, k, may be useful for a number of reasons. In one example, the coupling coefficient can be used to understand the arrangement of the coils relative to each other so tuning adjustments can be made to ensure adequate performance. If the receiver coil moves away from the transmitter coil, the mutual inductance will decrease, and ceteris paribus, less power will be transferred. In various embodiments, the system is configured to make tuning adjustments to compensate for the drop in coupling efficiency.

The exemplary system described above often has imperfect information. For various reasons as would be understood by one of skill in the art, the system does not collect data for all parameters. Moreover, because of the physical gap between coils and without an external means of communications between the two resonators, the transmitter may have information that the receiver does not have and vice versa. These limitations make it difficult to directly measure and derive the coupling coefficient, k, in real time.

Described below are several principles for estimating the coupling coefficient, k, for two coils of a given geometry. The approaches may make use of techniques such as Biot-Savart calculations or finite element methods. Certain assumptions and generalizations, based on how the coils interact in specific orientations, are made for the sake of simplicity of understanding. From an electric circuit point of view, all the physical geometry permutations can generally lead to the coupling coefficient.

Figure 2:
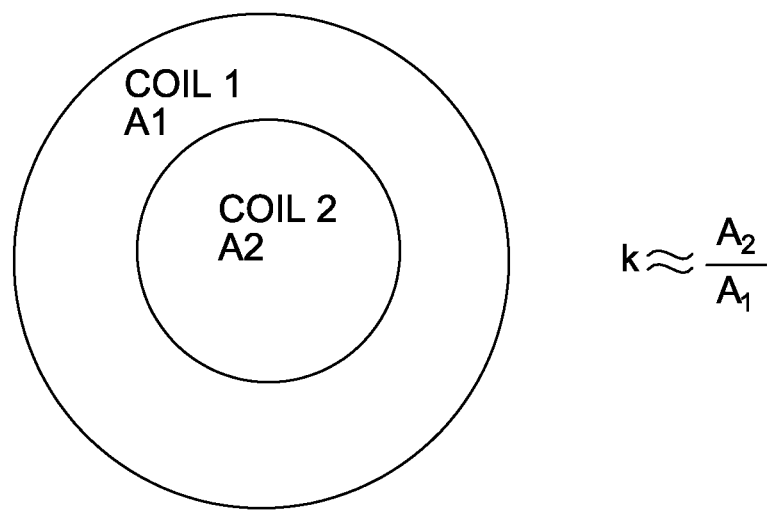
FIG. 2 illustrates the flux generated by a pair of coils.

If two coils are arranged so they are in the same plane, with one coil circumscribing the other, then the coupling coefficient can be estimated to be roughly proportional to the ratio of the area of the two coils. This assumes the flux generated by coil 1 is roughly uniform over the area it encloses as shown in FIG. 2.

Figure 3A:
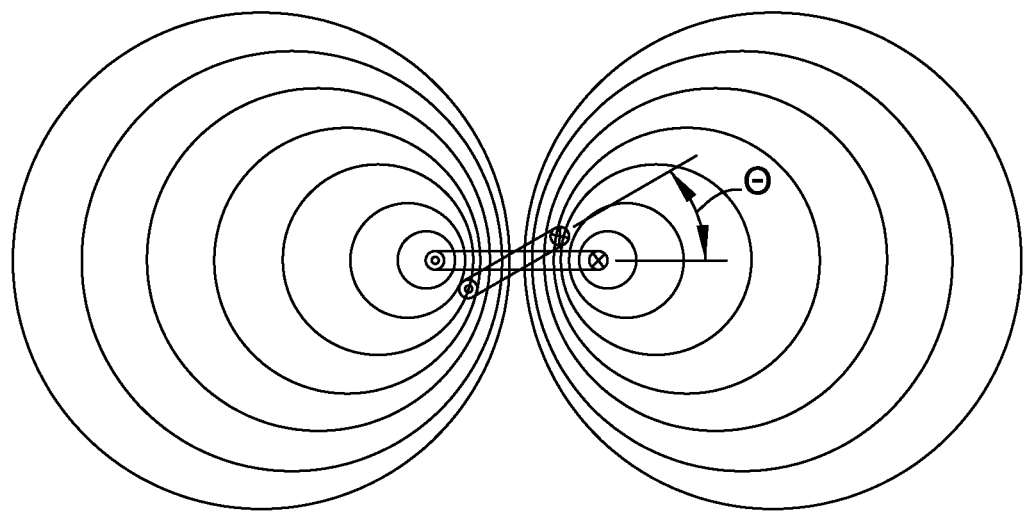
FIGS. 3A-3B illustrate the effect of coil alignment on the coupling coefficient.

If the coils are out of alignment such that the coils are at a relative angle, the coupling coefficient will decrease. The amount of the decrease is estimated to be about equal to the cosine of the angle as shown in FIG. 3A. If the coils are orthogonal to each other such that theta (θ) is 90 degrees, the flux will not be received by the receiver and the coupling coefficient will be zero.

Figure 3B:
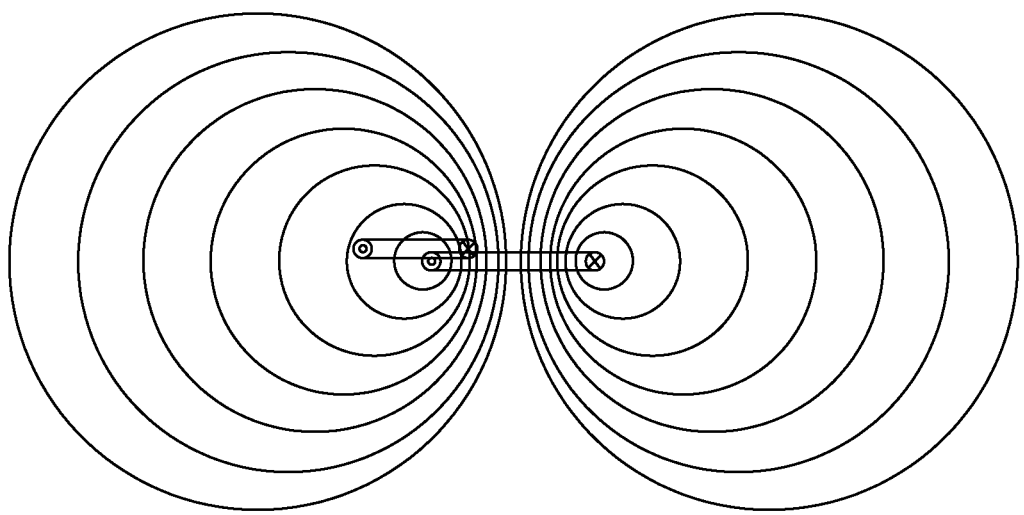

If the coils are arranged such that half the flux from one coil is in one direction and the other half is in the other direction, the flux cancels out and the coupling coefficient is zero, as shown in FIG. 3B.

A final principle relies on symmetry of the coils. The coupling coefficient and mutual inductance from one coil to the other is assumed to be the same regardless of which coil is being energized.

$$M_{xy} = M_{yx}$$

Figure 4:
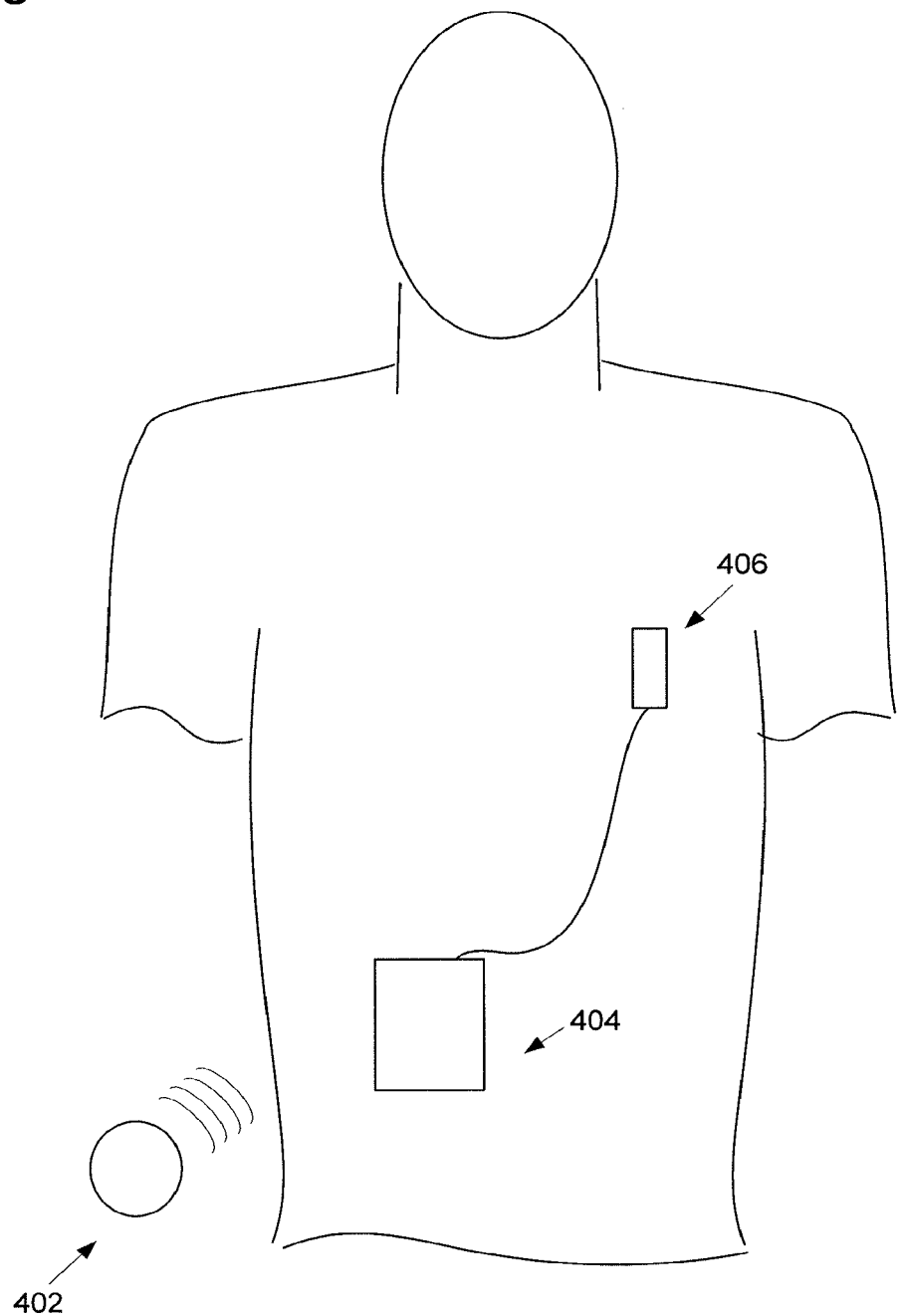
FIG. 4 illustrates on embodiment of a TET system.

As described above, a typical TET system can be subdivided into two parts, the transmitter and the receiver. Control and tuning may or may not operate on the two parts independently. FIG. 4 is a schematic diagram of a TET system having a wireless power transmitter 402 external to a patient with a wireless power receiver 404 and medical device 406 implanted within the patient. The transmitter 402 can be configured to transmit wireless power through the skin of the patient to the receiver 404, which can provide energy to the medical device 406, or charge a battery connected to the device 406.

TET systems are highly sensitive and susceptible to interference, for example, from other TET systems, metal objects, or objects with magnetic susceptibility. Accordingly, protections that can be implemented within a TET system to protect against adverse effects from these external factors. For example, the system can be configured to recognize significant influences and make adjustments accordingly. In another example, the system can indicate to a user (e.g. a patient) the presence of an undesirable factor so the user can take necessary precautions and/or move away from the influencing factor. Additionally, the external factors can be handled differently depending on the state of the implanted TET system. For example, how the system reacts to an external factor during wireless power transmission may be different than how the system reacts when there is not an external transmitter sending wireless power to the receiver implanted in the patient. In another embodiment, the system may react differently depending on the charge state of the implanted battery.

In various embodiments, the system utilizes a troubleshooting algorithm such that, if the system performs unexpectedly, the algorithm can be implemented to help a user, technician, and/or clinician determine if the cause is due to a fault in a system component, the presence of an unexpected external factor, and/or improper tuning and adjustment of the system. In one example in which the TET system is used in conjunction with a VAD, the clinician may notice during a regular visit that the VAD is not providing sufficient circulatory support. The clinician then needs to determine if the pump is not working properly, if the power needs to be increased, or if the user has been around factors that are negatively affecting the system (e.g. the patient's TET system is regularly exposed to a large number of ferromagnetic materials). An example of a troubleshooting algorithm for assisting a clinician with troubleshooting an implantable medical device without requiring explant is described in U.S. Pub. No. US 2011/0313238 A1, incorporated herein for all purposes by reference.

The possible solutions involve, but are not limited to, (i) adjusting tuning to compensate for the external interference, (ii) turning off the transmitter if powered by a battery and the energy losses are great, (iii) setting off an alarm to the patient to notify the patient of the external interference, (iv) a combination of (i) and (iii), or (v) a combination of (ii) and (iii). These solutions can be implemented with hardware and/or software on either the transmitter or the receiver or both. In one embodiment, the TET system can set off an alarm and adjust tuning to compensate for the external factor. The patient alarm can be visual, audible, vibratory, etc. The alarm can also be internal to another component in the system, e.g., the alarm can be configured to trigger the transmitter to stop transmitting for a pre-set period of time.

Figure 5:
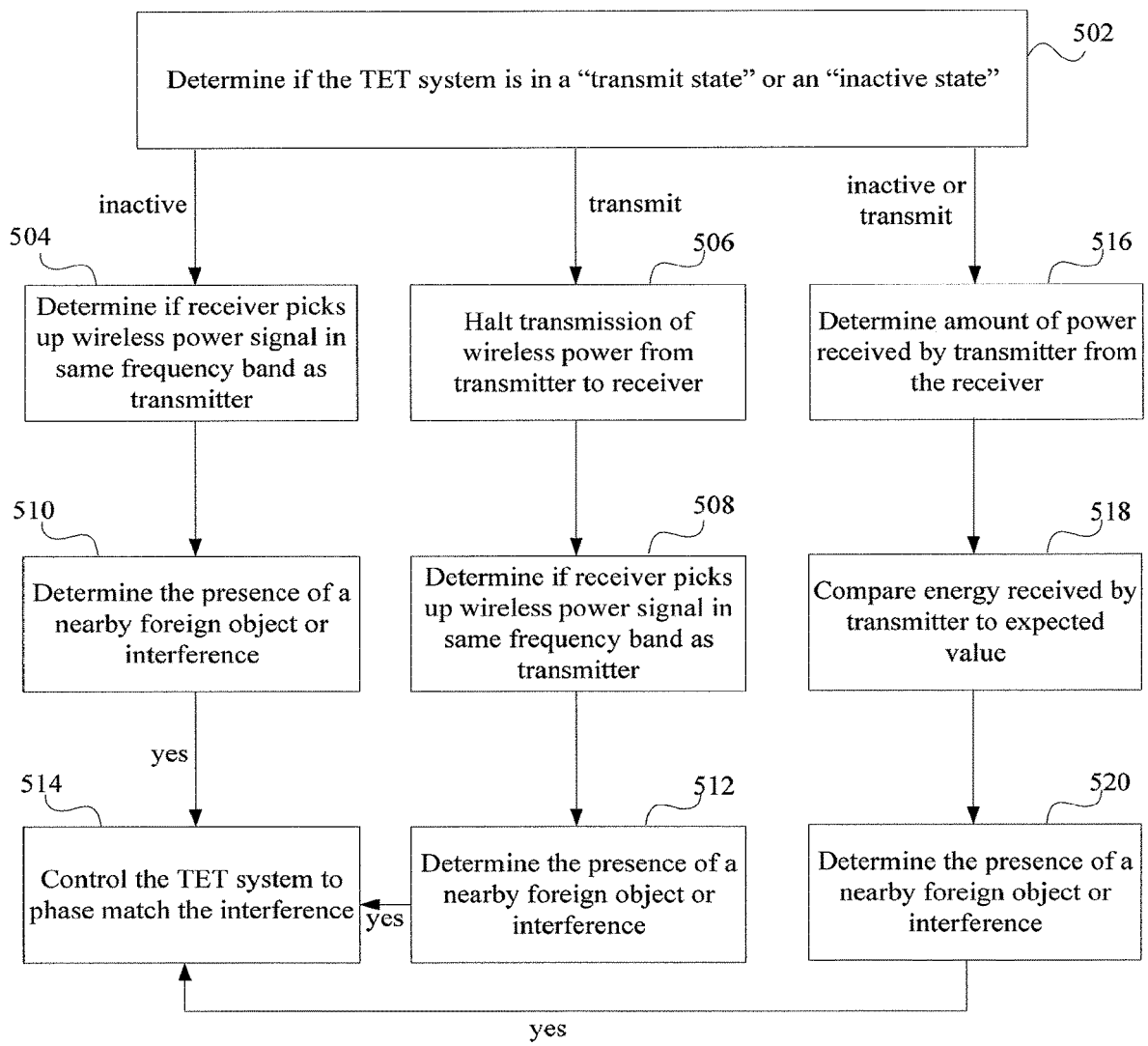
FIG. 5 is a flowchart illustrating one method of utilizing a protective algorithm in a TET system.

FIG. 5 illustrates a flowchart that explains the use of a protective algorithm by a TET system, such as the system shown in FIG. 4. Referring to step 502 of FIG. 5, first, the TET system can be classified as being in one of two energy states. A "transmit state" can be when a transmitter of the TET system is transmitting wireless power to a receiver implanted in a patient. An "inactive state" can be when no transmission of power is occurring, e.g., the patient is not attempting to transmit power from a transmitter to the receiver. It should be understood though, that in the scenario where a patient is in proximity to another transmitter (such as another patient's transmitter) that inadvertent power transfer may occur without proper protections in place.

Once the power state has determined, a TET system according to one embodiment can include a system or method to detect the presence of another TET system or external interference. If the TET system is in an "inactive state", then in step 504 of FIG. 5 the TET system can determine if the receiver picks up any wireless power signals in the same frequency band as the TET system operates in. Similarly, if the TET system is in a "transmit state", transmission of wireless power from the transmitter to the receiver can be halted at step 506, and then at step 508 the TET system can determine if the receiver picks up any wireless power signals in the same frequency band as the TET system operates in.

If the TET system determines in either step 504 or step 508 that the receiver is picking up interfering wireless power signals in the same frequency band as the transmitter, the TET system can determine in steps 510 and 512 that the TET system is in the presence of nearby interference, such as another TET system transmitting wireless power nearby. In some embodiments, the TET system can indicate to a user that there is a nearby interference. This indication can be in the form of an audible indicator (e.g., a beep, alarm, etc). a visual indicator (e.g., a light on the transmitter, a warning on a display of the transmitter, etc), or in the form of a message to the user or to a physician (e.g., an email or text message alert).

In some embodiments, the TET system can be configured at step 506 to temporarily halt transmission of power at predetermined periods. The frequency of the "temporary halts" can be based on the receiver's ability to determine the frequency of an induced voltage, to ensure that the phase lock will not slip out of sync.

In embodiments where a separate transmitting TET system is detected nearby, at step 514 of FIG. 5 the transmitter of the TET system can be controlled to phase match to the interference or other transmitter of the separate TET system to compensate for the interference. Note that if the separate TET system follows the same procedure, it will, during a temporary halt in its "transmit state", detect the first TET system and continue the phase match.

In another embodiment when the TET system is in either an "inactive state" or a "transmit state", referring to step 516, one approach can be to check how much power the transmitter is receiving. If the TET system is in the "transmit state", the transmitter can determine how much energy is coming back to the transmitter from the receiver, and compare this amount to calculated or tabulated values of how much power should be expected under current operating conditions. If an excess amount of energy is coming back compared to the amount that is expected, this is an indicator that another transmitter is nearby and the system can determine the presence of a nearby interference at step 520 of FIG. 5. Similarly, if the transmitter is in an "inactive state" and the receiver is still picking up some magnetic field, the TET system can use this information to interpret the interfering external factor. Again, in both these scenarios, the next step would be to match phase with the other transmitter and/or indicate the interference to the user.

Whichever of the above algorithms is used, an alert can be provided to the user to indicate that a foreign source has been detected and has been phase matched. In one embodiment, the alert is upgraded to an alarm status if phase matching cannot be accomplished, because it means either that some of the wireless power transmitted by the transmitter is being sent to another system or that the receiver could be receiving net energy. The former is undesirable, particularly if the transmitter is operating off a battery source, as some energy is lost from the system. The latter is not bad in itself, but could become a concern if the foreign transmitter "gives away" more energy than the receiver can handle.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A wireless power transfer system, comprising:
    a transmit resonator configured to transmit wireless power in a frequency band;
    a receive resonator configured to be implanted in a human patient, the receive resonator further configured to receive wireless power from the transmit resonator; and
    a controller coupled to the transmit resonator and configured to:
        determine the presence of interference that is capable of affecting transmission of wireless power from the transmit resonator to the receive resonator by:
            temporarily halting transmission of power from the transmit resonator to the receive resonator during predetermined periods; and
            determining, during the predetermined periods when the transmission of power is temporarily halted, that the receive resonator is picking up wireless power signals in the same frequency band that the transmit resonator uses;
        generate an alert to notify a user of the interference; and
        control the wireless power transfer system to address the interference.

2. The wireless power transfer system according to claim 1, wherein to generate an alert, the controller is configured to generate at least one of an audible indicator and a visual indicator.

3. The wireless power transfer system according to claim 1, wherein to generate an alert, the controller is configured to transmit at least one of an email and a text message.

4. The wireless power transfer system according to claim 1, wherein to control the wireless power transfer system, the controller is configured to tune at least one of the transmit resonator and the receive resonator to compensate for the interference.

5. The wireless power transfer system according to claim 1, wherein to control the wireless power transfer system, the controller is configured to deactivate the transmit resonator.

6. The wireless power transfer system according to claim 1, wherein the interference is an additional transmit resonator.

7. A method of operating a wireless power transfer system including a transmit resonator and a receive resonator, said method comprising:
    determining the presence of interference that is capable of affecting transmission in a frequency band of wireless power from the transmit resonator to the receive resonator by:
        temporarily halting transmission of power from the transmit resonator to the receive resonator during predetermined periods; and
        determining, during the predetermined periods when the transmission of power is temporarily halted, that the receive resonator is picking up wireless power signals in the same frequency band that the transmit resonator uses;
    generating an alert to notify a user of the interference; and
    controlling the wireless power transfer system to address the interference.

8. The method of claim 7, wherein generating an alert comprises generating at least one of an audible indicator and a visual indicator.

9. The method of claim 7, wherein generating an alert comprises transmitting at least one of an email and a text message.

10. The method of claim 7, wherein controlling the wireless power transfer system comprises tuning at least one of the transmit resonator and the receive resonator to compensate for the interference.

11. The method of claim 7, wherein controlling the wireless power transfer system comprises deactivating the transmit resonator.

* * * * *